(12) United States Patent
Hu et al.

(10) Patent No.: US 11,311,481 B2
(45) Date of Patent: Apr. 26, 2022

(54) INJECTABLE AND SHEARING-THINNING MICROBEADS GEL, USE THEREOF, AND METHOD FOR PREPARING THE SAME

(71) Applicant: National Tsing Hua University, Hsinchu (TW)

(72) Inventors: Shang-Hsiu Hu, Hsinchu (TW); Ru-Siou Hsu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 159 days.

(21) Appl. No.: 16/550,750

(22) Filed: Aug. 26, 2019

(65) Prior Publication Data
US 2020/0121597 A1 Apr. 23, 2020

(30) Foreign Application Priority Data
Oct. 19, 2018 (TW) .................................. 107137070

(51) Int. Cl.
*A61K 9/50* (2006.01)
*A61K 9/06* (2006.01)
*A61K 9/16* (2006.01)
*A61K 9/00* (2006.01)
*A61P 17/02* (2006.01)
*A61P 25/00* (2006.01)

(52) U.S. Cl.
CPC .............. *A61K 9/06* (2013.01); *A61K 9/0019* (2013.01); *A61K 9/1652* (2013.01); *A61K 9/1658* (2013.01); *A61K 9/1682* (2013.01); *A61P 17/02* (2018.01); *A61P 25/00* (2018.01)

(58) Field of Classification Search
None
See application file for complete search history.

(56) References Cited

U.S. PATENT DOCUMENTS

| 5,540,927 A | * | 7/1996 | Jason ..................... B01J 13/02 424/408 |
| 7,700,819 B2 | | 4/2010 | Ambrosio et al. |
| 2008/0226722 A1 | | 9/2008 | Van Tomme et al. |

FOREIGN PATENT DOCUMENTS

| CN | 105113053 A | 12/2015 |
| CN | 105796478 A | 7/2016 |
| CN | 107007881 A | 8/2017 |
| EP | 1982700 A1 | 10/2008 |
| TW | 200845948 | 12/2008 |

OTHER PUBLICATIONS

Chen, " The Preliminary Study of Constructing Injectable Scaffolds via Self-assembling of Natural Polysaccharides Microspheres", Masters' Thesis, Jun. 5, 2010, pp. 1-103, Jinan University, China.
Chen et al., "3D bioprinted multiscale composite scaffolds based on gelatin methacryloyl (GelMA)/chitosan microspheres as a modular bioink for enhancing 3D neurite outgrowth and elongation", Journal of Colloid and Interface Science, Apr. 9, 2020, pp. 162-173, vol. 574.
Van Tomme et al., "Effect of particle size and charge on the network properties of microsphere-based hydrogels", European Journal of Pharmaceutics and Biopharmaceutics, Jun. 6, 2008, pp. 522-530, vol. 70.

* cited by examiner

*Primary Examiner* — Susan T Tran
(74) *Attorney, Agent, or Firm* — The Webb Law Firm

(57) ABSTRACT

The present disclosure provides an injectable and shearing-thinning microbeads gel including a first microgel and a second microgel. The first microgel has a first electric charge and includes a plurality of first gel microspheres. The second microgel has a second electric charge and includes a plurality of second gel microspheres. The first electric charge is opposite to the second electric charge, the average particle size of the first gel microspheres is equal to the average particle size of the second gel microspheres, each of the first gel microspheres includes an acrylic chitosan polymer, an acrylic silk polymer, or a combination thereof, and each of the second gel microspheres includes an acrylic gelatin polymer, an acrylic hyaluronic acid polymer, an acrylic alginate polymer, or a combination thereof.

7 Claims, 12 Drawing Sheets
(1 of 12 Drawing Sheet(s) Filed in Color)

INJECTABLE AND SHEARING-THINNING MICROBEADS GEL, USE THEREOF, AND METHOD FOR PREPARING THE SAME

CROSS-REFERENCE TO RELATED APPLICATION

This application claims priority to Taiwanese Application No. 107137070 filed Oct. 19, 2018, the disclosure of which is hereby incorporated by reference in its entirety.

BACKGROUND

Technical Field

The present disclosure relates to a medical hydrogel and a preparing method thereof. More particularly, the present disclosure relates to an injectable medical hydrogel and a preparing method thereof.

Description of Related Art

Tissue engineering is a medical method that bioactive substances are cultured in vitro and then transplanted into living organisms so as to achieve the aims of cell regeneration and tissue repair. Cells, cell growth scaffold and bioreactors are three essential components of tissue engineering, in which cell growth scaffold is the major focus of related research. Cell growth scaffold is made of biodegradable materials. In addition to high biocompatibility and porosity, the cell growth scaffold must have enough mechanical strength so as to promote cells attaching and growing therein.

In order to maintain mechanical strength and porous structure, the conventional cell growth scaffold must be transplanted into the human body by an invasive manner such as surgery. However, surgery and other invasive transplanted methods may cause additional damage to the human body, and the risk of infection may be further increased. Accordingly, the application efficiency of the conventional cell growth scaffold is not as good as expected. In order to solve the aforementioned problems, researchers in the related art provide a gel which can be transplanted into the human body by an injection method and for cell attachment and growth. However, the oxygen and nutrient exchange rate between the peripheral cells and the aforementioned gel may be inefficient due to the porosity of the aforementioned gel is insufficient. Thus, the cell growth activity may be decreased, and even worse, the cells may be aging or death, resulting in failure of cell transplantation.

Therefore, how to develop a cell growth scaffold having high biocompatibility, porosity, mechanical strength and use convenience has become the major aims of related academic and industry.

SUMMARY

According to one aspect of the present disclosure, a method for preparing an injectable and shearing-thinning microbeads gel includes the following steps: a first gel microsphere preparing step is performed, a second gel microsphere preparing step is performed, and a mixing step is performed. The first gel microsphere preparing step includes the following steps. A first solution is provided, wherein the first solution is used as a water phase and includes a first component and a second component, the first component includes an acrylic acid compound or a derivative thereof, and the second component includes a chitosan oligomer or a silk. A first oil-phase solution is provided. A first water-in-oil emulsification is performed by mixing the first solution and the first oil-phase solution so as to form a plurality of first gel microspheres. The second gel microsphere preparing step includes the following steps. A second solution is provided, wherein the second solution is used as a water phase and includes a third component and a fourth component, the third component includes an acrylic acid compound or a derivative thereof, and the fourth component includes a gelatin, a hyaluronic acid or an alginate. A second oil-phase solution is provided. A second water-in-oil emulsification is performed by mixing the second solution and the second oil-phase solution so as to form a plurality of second gel microspheres. The mixing step mixes the first gel microspheres, the second gel microspheres and an aqueous solution so as to obtain the injectable and shearing-thinning microbeads gel. Wherein each of the first gel microspheres has a first electric charge, each of the second gel microspheres has a second electric charge, and the first electric charge is opposite to the second electric charge.

According to another aspect of the present disclosure, an injectable and shearing-thinning microbeads gel includes a first microgel and a second microgel. The first microgel has a first electric charge and includes a plurality of first gel microspheres, wherein an average particle size of the first gel microspheres ranges from 30 µm to 500 µm. The second microgel has a second electric charge and includes a plurality of second gel microspheres, wherein an average particle size of the second gel microspheres ranges from 30 µm to 500 µm. Wherein the first electric charge is opposite to the second electric charge, the average particle size of the first gel microspheres is equal to the average particle size of the second gel microspheres, each of the first gel microspheres includes an acrylic chitosan polymer, an acrylic silk polymer, or a combination thereof, and each of the second gel microspheres includes an acrylic gelatin polymer, an acrylic hyaluronic acid polymer, an acrylic alginate polymer, or a combination thereof.

According to further another aspect of the present disclosure, a method for promoting a tissue repair includes administering the aforementioned injectable and shearing-thinning microbeads gel to a subject in need for the tissue repair.

According to still another aspect of the present disclosure, a method for promoting a nerve cell growth includes administering the aforementioned injectable and shearing-thinning microbeads gel to a subject in need for a treatment of a nerve damage.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows.

DETAILED DESCRIPTION

<Method for Preparing an Injectable and Shearing-Thinning Microbeads Gel>

Figure 1:
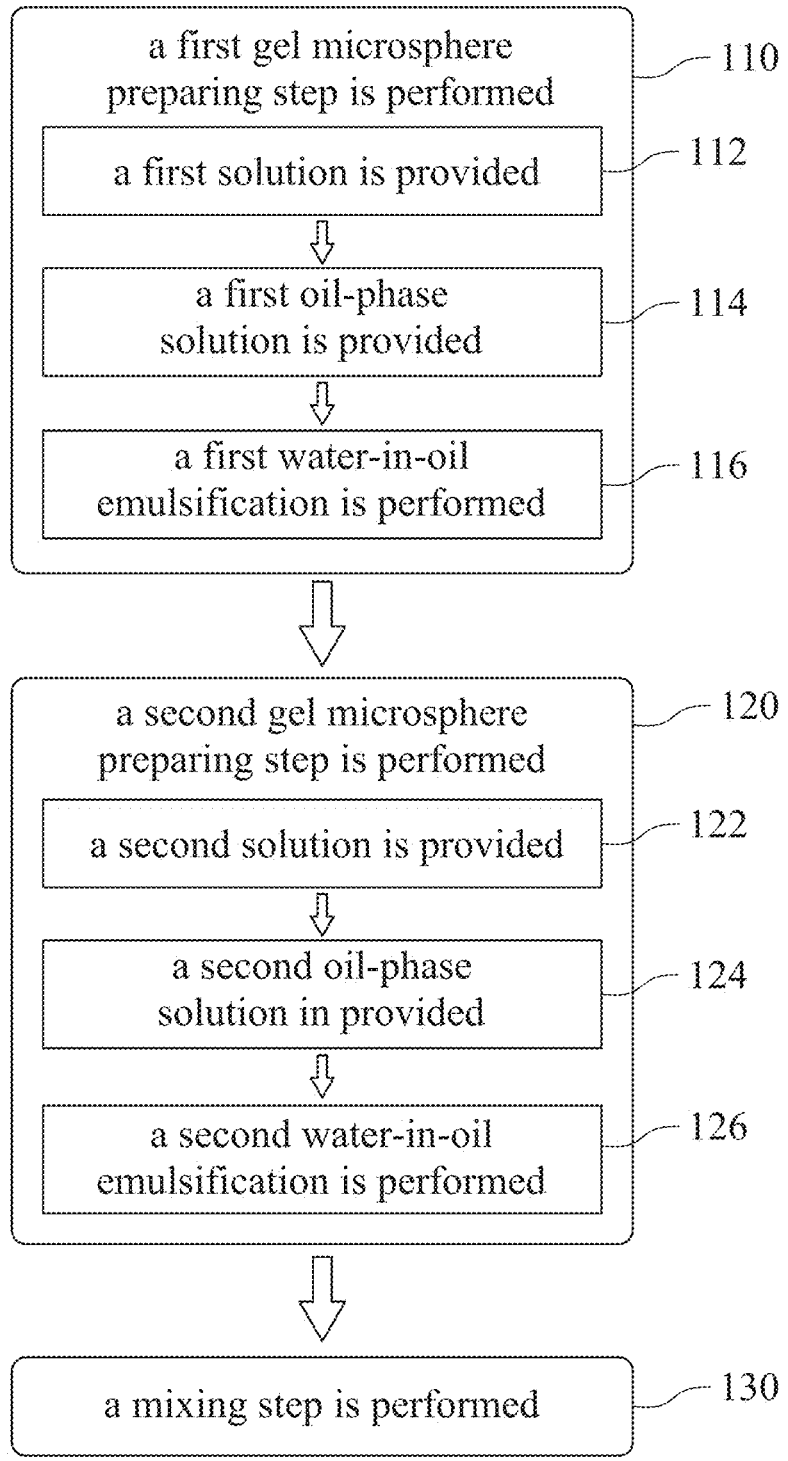
FIG. 1 is a flow chart of a method for preparing an injectable and shearing-thinning microbeads gel according to the present disclosure.

Please refer to FIG. 1, which is a flow chart of a method 100 for preparing an injectable and shearing-thinning microbeads gel according to the present disclosure. The method 100 for preparing an injectable and shearing-thinning microbeads gel includes Step 110, Step 120 and Step 130.

In Step 110, a first gel microsphere preparing step is performed, wherein the first gel microsphere preparing step includes Step 112, Step 114 and Step 116.

In Step 112, a first solution is provided, wherein the first solution is used as a water phase and includes a first component and a second component. The first component includes an acrylic acid compound or a derivative thereof, and the second component includes a chitosan oligomer or a silk. More preferably, the acrylic acid compound or the derivative thereof can include methacrylic acid, methacrylic anhydride, glycidyl methacrylate or monomers of polymeric materials containing double bonds. Thus, a better structural strength of the first gel microsphere can be obtained.

In Step 114, a first oil-phase solution is provided. In particular, the first oil-phase solution can include an oily solution and a surfactant, wherein the surfactant can be but not limited to polyvinyl alcohol (PVA), tween 20, tween 80 or sodium dodecyl sulfate (SDS) so as to enhance the polymerization efficiency of the first component and the second component in the first solution.

In Step 116, a first water-in-oil emulsification is performed by mixing the first solution and the first oil-phase solution so as to form a plurality of first gel microspheres, wherein each of the first gel microspheres has a microspherical structure. More preferably, the first water-in-oil emulsification can be performed in a microfluidic channel system, and an average particle size of the first gel microspheres can range from 30 μm to 500 μm by adjusting the flow velocities of the first solution used as the water phase and the first oil-phase solution as well as the channel sizes of the microfluidic channel system. Therefore, it is favorable for maintaining a lower molecular weight polydispersity.

In Step 120, a second gel microsphere preparing step is performed. The second gel microsphere preparing step includes Step 122, Step 124 and Step 126.

In Step 122, a second solution is provided, wherein the second solution is used as a water phase and includes a third component and a fourth component. The third component includes an acrylic acid compound or a derivative thereof, and the fourth component includes a gelatin, a hyaluronic acid or an alginate.

In Step 124, a second oil-phase solution in provided. In particular, the second oil-phase solution can include an oily solution and a surfactant, wherein the surfactant can be but not limited to polyvinyl alcohol (PVA), tween 20, tween 80 or sodium dodecyl sulfate (SDS) so as to enhance the polymerization efficiency of the third component and the fourth component in the second solution.

In Step 126, a second water-in-oil emulsification is performed by mixing the second solution and the second oil-phase solution so as to form a plurality of second gel microspheres, wherein each of the second gel microspheres has a microspherical structure. More preferably, the second water-in-oil emulsification can be performed in a microfluidic channel system, and an average particle size of the second gel microspheres can range from 30 μm to 500 μm by adjusting the flow velocities of the second solution used as the water phase and the second oil-phase solution as well as the channel sizes of the microfluidic channel system. Therefore, it is favorable for maintaining a lower molecular weight polydispersity.

Furthermore, the degree of substitution of functional groups (such as amino groups, hydroxyl groups) of the first gel microspheres and the second gel microspheres can be arranged by a modification method so as to adjust a first electric charge of each of the first gel microspheres and a second electric charge of each of the second gel microspheres. Furthermore, biomolecules such as cell growth factors and cell attachment peptides can be connected to the first gel microspheres and the second gel microspheres by a photo-crosslinking reaction triggered by photo-activated free radical initiators and UV light so as to enhance the application range of the first gel microspheres and the second gel microsphere.

In Step 130, a mixing step is performed, wherein the mixing step mixes the first gel microspheres, the second gel microspheres and an aqueous solution so as to obtain the injectable and shearing-thinning microbeads gel of the present disclosure. In detail, because the functional groups of the second component of the first gel microsphere are different from the functional groups of the fourth component of the second gel microsphere, each of the first gel microspheres prepared by Step 110 has the first electric charge, and each of the second gel microspheres prepared by Step 120 has the a second electric charge. The first electric charge is opposite to the second electric charge, and the average particle size of the first gel microsphere is equal to the average particle size of the second gel microsphere. Specifically, the injectable and shearing-thinning microbeads gel prepared by the aforementioned method can be a moldable and deformable gel due to the electrostatic attraction between the first gel microspheres and the second gel microspheres and then neatly arranged therewith, and the injectable and shearing-thinning microbeads gel of the present disclosure can be re-adjusted and assembled by the electrostatic attraction between the first gel microspheres and the second gel microspheres and the shear thinning force thereof so as to make it injectable.

More preferably, the first gel microspheres and the second gel microspheres of the injectable and shearing-thinning microbeads gel can be contained in a volume ratio of 1:0.5 to 1:6, and a first microgel and a second microgel of the injectable and shearing-thinning microbeads gel can be contained in a volume ratio of 1:0.5 to 1:6, so that it is favorable for adjusting a gel strength of the injectable and shearing-thinning microbeads gel of the present disclosure. Furthermore, the gel strength of the injectable and shearing-thinning microbeads gel can range from 30 Pa to 3100 Pa, an average porosity of the injectable and shearing-thinning microbeads gel can range from 35% to 50%, and an average pore size of the injectable and shearing-thinning microbeads gel can range from 30 μm to 90 μm.

The method 100 for preparing an injectable and shearing-thinning microbeads gel will be further described by the following embodiments, and the physical property and the efficiency of the injectable and shearing-thinning microbeads gel will also be described by a plurality of embodiments and comparative embodiments. However, the spirit and scope of the appended claims should not be limited to the description of the embodiments contained herein.

Embodiments

I. Prepare the Injectable and Shearing-Thinning Microbeads Gel

In one embodiment of the present disclosure, the injectable and shearing-thinning microbeads gel includes a first microgel and a second microgel, wherein the first microgel has a first electric charge and includes a plurality of first gel microspheres, the second microgel has a second electric charge and includes a plurality of second gel microsphere, and the first electric charge is opposite to the second electric charge. The details of preparing the first gel microsphere, the second gel microsphere and mixing the first gel microspheres and the second gel microspheres will be described as follow.

1. Prepare the First Gel Microspheres

According to the difference of the first component and the second component, the first gel microspheres can be classified into the acrylic chitosan polymer and the acrylic silk polymer. In the present embodiment, the acrylic chitosan polymer can be methacrylate-modified chitosan ("Chito-MA" hereafter), the acrylic silk polymer can be methacrylate-modified silk ("Sil-MA" hereafter), and the preparing method of the first gel microspheres with different component are described as follow.

(1) Prepare First Gel Microspheres Made of Chito-MA

First, 1.5 g of water-soluble chitin is added into 50 mL of phosphate buffered saline (PBS) and stirred at 60° C. until dissolved completely. Next, an appropriate amount of methacrylic anhydride (MA) is added dropwise to the aforementioned solution including the water-soluble chitin at a rate of 0.5 mL/min and stirred continuously for 3 hours in a 50° C. thermostat so as to react completely. After reacting for 3 hours, 200 mL of 50° C. PBS is added for dilution and then stirred continuously until the reaction is terminated. Then, the aforementioned solution is placed in a dialysis bag and dialyzed using a 12-14 kDa medium cut-off (MCO) membrane at 50° C. with pure water, and then the dialyzed solution is placed into a centrifuge tube and centrifuged at 2500 rpm for 15 minutes. Next, the precipitate thereof will be removed so as to obtain a first solution including the pre-polymer of Chito-MA, and a first oil-phase solution including an oily solution and a surfactant is added therein so as to form a plurality of first gel microspheres made of Chito-MA.

(2) Prepare the First Gel Microsphere Made of Sil-MA

First, 20 g of degummed silk fiber is added into 100 mL, 60° C. of lithium bromide solution with a concentration of 9.3 M and then reacted for 1 hour. Next, 2 mL, 4 mL, 6 mL and 10 mL (with concentrations of 141 mM, 282 mM, 424 mM and 705 mM, respectively) of glycidyl methacrylate (GMA) are added into the aforementioned solution including the degummed silk fiber and reacted at 60° C., 300 rpm for 3 hours. After the aforementioned reaction is completed, the aforementioned solution is filtered with Miracloth Filter (Calbiochem, San Diego, USA) and is dialyzed using a cut-off dialysis tube with 12-14 kDa medium cut-off membrane at 50° C. with distilled water so as to obtain a first solution including the pre-polymer of Sil-MA. Then, a first oil-phase solution including an oily solution and a surfactant is added to the first solution so as to form a plurality of first gel microspheres made of Sil-MA.

In the present embodiment, a first water-in-oil emulsification thereof is performed in a microfluidic system, and an average particle size of the first gel microspheres can range from 30 μm to 500 μm by adjusting the ratio of the first solution and the first oil-phase solution, the flow velocities thereof and the channel sizes of the microfluidic channel system. Therefore, it is favorable for maintaining a lower molecular weight polydispersity.

2. Prepare the Second Gel Microspheres

According to the difference of the third component and the fourth component, the second gel microspheres can be classified into the acrylic gelatin polymer, the acrylic hyaluronic acid polymer and the acrylic alginate polymer. In the present embodiment, the acrylic gelatin polymer can be methacrylate-modified gelatin ("Gel-MA" hereafter), the acrylic hyaluronic acid polymer can be methacrylate-modified hyaluronic acid ("HA-MA" hereafter), the acrylic alginate polymer can be methacrylate-modified alginate ("Algi- MA" hereafter), and the preparing method of the second gel microspheres with different component are described as follow.

(1) Prepare the Second Gel Microsphere Made of Gel-MA

First, 5 g of gelatin is added into 50 mL of PBS and stirred at 60° C. until dissolved completely. Next, an appropriate amount of methacrylic anhydride is added dropwise to the aforementioned solution including the gelatin at a rate of 0.5 mL/min and stirred continuously for 3 hours in a 50° C. thermostat so as to react completely. After reacting for 3 hours, 200 mL of 50° C. PBS is added for dilution and then stirred continuously until the reaction is terminated. Then, the aforementioned solution is placed in a dialysis bag and dialyzed using a 12-14 kDa medium cut-off membrane at 50° C. with pure water, and then the dialyzed solution is placed into a centrifuge tube and is centrifuged at 2500 rpm for 15 minutes. Next, the precipitate thereof will be removed so as to obtain a second solution including the pre-polymer of Gel-MA, and a second oil-phase solution including an oily solution and a surfactant is added therein so as to form a plurality of second gel microsphere made of Gel-MA.

(2) Prepare the Second Gel Microsphere Made of HA-MA

First, 0.5 g of hyaluronic acid is added into 50 mL of distilled water and stirred at a room temperature overnight. Next, 1 mL of trimethylamine (TEA) solution, 1 mL of glycidyl methacrylate solution with a purity greater than 92% and 1 g of tetrabutylammonium bromide (TBAB) are added into the aqueous solution including the hyaluronic acid and stirred continuously at 55° C. for 1 hour. After reacting for 1 hour and cooling thereof, the aforementioned aqueous solution is progressed two extraction-precipitation steps in acetone, and the precipitate thereof is dried and then re-dissolved in distilled water. Next, the aforementioned solution is dialyzed using a cut-off dialysis tube with 12-14 kDa medium cut-off membrane at 50° C. with distilled water so as to obtain a second solution including the pre-polymer of HA-MA. Then, a second oil-phase solution including an oily solution and a surfactant is added to the second solution so as to form a plurality of second gel microspheres made of HA-MA.

(3) Prepare the Second Gel Microsphere Made of Algi-MA

First, 4.0 g of alginate is added into 200 mL of distilled water and stirred until dissolved completely. Next, 15 mL of methacrylic anhydride with a weight ratio of 2.0% is added therein all at once. Then, the solution is adjusted to the condition of pH=8 and then reacted at 5° C. for 24 hours. After reacting for 24 hours, the aforementioned solution is purified by ethanol and then dried under vacuum for 3 days at room temperature. The dried product after drying is re-dissolved in distilled water and dialyzed using a cut-off dialysis tube with 12-14 kDa medium cut-off membrane with distilled water so as to obtain a second solution including the pre-polymer of Algi-MA. Then, a second oil-phase solution including an oily solution and a surfactant is added to the second solution so as to form a plurality of second gel microspheres made of HA-MA.

In the present embodiment, a second water-in-oil emulsification thereof is performed in a microfluidic system, and an average particle size of the second gel microspheres can range from 30 μm to 500 μm by adjusting the ratio of the second solution and the second oil-phase solution, the flow velocities thereof and the channel sizes of the microfluidic channel system. Therefore, it is favorable for maintaining a lower molecular weight polydispersity.

3. Mix the First Gel Microspheres and the Second Gel Microsphere

After finishing the preparation of the first gel microspheres and the second gel microspheres, the first gel microspheres and the second gel microspheres are mixed in a volume ratio of 1:0.5 to 1:6 and then an aqueous solution is added therein, wherein the average particle size of the first gel microspheres is equal to the average particle size of the second gel microspheres so as to obtain the injectable and shearing-thinning microbeads gel of the present disclosure.

Figure 2:
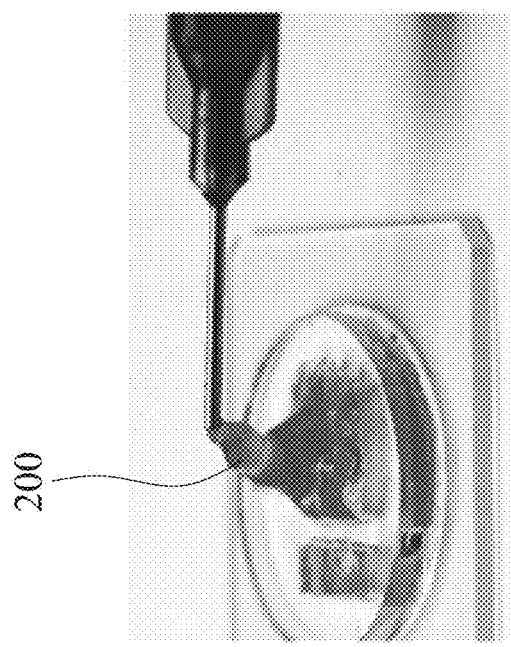
FIG. 2 is an image of the injectable and shearing-thinning microbeads gel according to the present disclosure.

Please refer to FIG. 2. FIG. 2 is an image of the injectable and shearing-thinning microbeads gel 200 according to the present disclosure. As shown in FIG. 2, the injectable and shearing-thinning microbeads gel 200 is a colloid that can be injected through a needle and can self-assemble to form a colloidal form after discharging from the needle without applying an external force, and the injectable and shearing-thinning microbeads gel 200 discharged from the needle can be further shaped into a specific pattern. Accordingly, the injectable and shearing-thinning microbeads gel 200 can self-assemble after being injected into a cavity with complex conformation, such as a bone clearance and a tissue gap, and the shape of the injectable and shearing-thinning microbeads gel 200 can be adjusted according to actual needs. Therefore, the injectable and shearing-thinning microbeads gel 200 has excellent use convenience and broad application.

In particular, in the examples of the present disclosure, the first gel microspheres are Chito-MA gel microspheres with positive electric charge, and the second gel microspheres are Gel-MA gel microspheres with negative electric charge. In detail, the first gel microspheres and the second gel microspheres of the injectable and shearing-thinning microbeads gel of Example 1 are contained in a volume ratio of 1:1, the first gel microspheres and the second gel microspheres of the injectable and shearing-thinning microbeads gel of Example 2 are contained in a volume ratio of 1:2, and the first gel microspheres and the second gel microspheres of the injectable and shearing-thinning microbeads gel of Example 3 are contained in a volume ratio of 1:5. The physical property, the biocompatibility and the ability to promote nerve cell proliferation of the injectable and shearing-thinning microbeads gels of Example 1 to Example 3 will be further evaluated in the following experiments.

II. Evaluate the Physical Property of the Injectable and Shearing-thinning Microbeads Gel of the Present Disclosure 1. Evaluate the Gel Strength and the Shear-thinning Property of the Injectable and Shearing-Thinning Microbeads Gel of the Present Disclosure The gel strength of the injectable and shearing-thinning microbeads gel of the present disclosure is evaluated by the rheological properties of the injectable and shearing-thinning microbeads gels of Example 1 to Example 3. In the test, storage modulus (G') and loss modulus (G") of the injectable and shearing-thinning microbeads gels of Example 1 to Example 3 are measured by the rheometer (AR 2000ex, TA Instruments) using a flat steel plate geometry (20 mm diameter) at 25° C. with a gap distance of 500 mm, a constant stress is 1 Pa and a constant frequency is 1 Hz. The storage modulus is also known as elastic modulus, which is a stored amount of energy when the material is elastically deformed and for presenting the elasticity thereof, and the loss modulus is also known as viscosity modulus, which is a stored amount of energy when the material is viscously deformed and for presenting the viscosity thereof. Therefore, in the present test, the gel strength of the injectable and shearing-thinning microbeads gel of the present disclosure will be evaluated by the measured values of the storage modulus and the loss modulus.

Furthermore, the present test further includes Comparative example 1 and Comparative example 2, wherein Comparative example 1 is a conventional hydrogel with positive electric charge, and Comparative example 2 is a conventional hydrogel with negative electric charge so as to compare the gel strength of the injectable and shearing-thinning microbeads gel of the present disclosure with the gel strength of the hydrogels of Comparative example 1 and Comparative example 2.

Figure 3A:
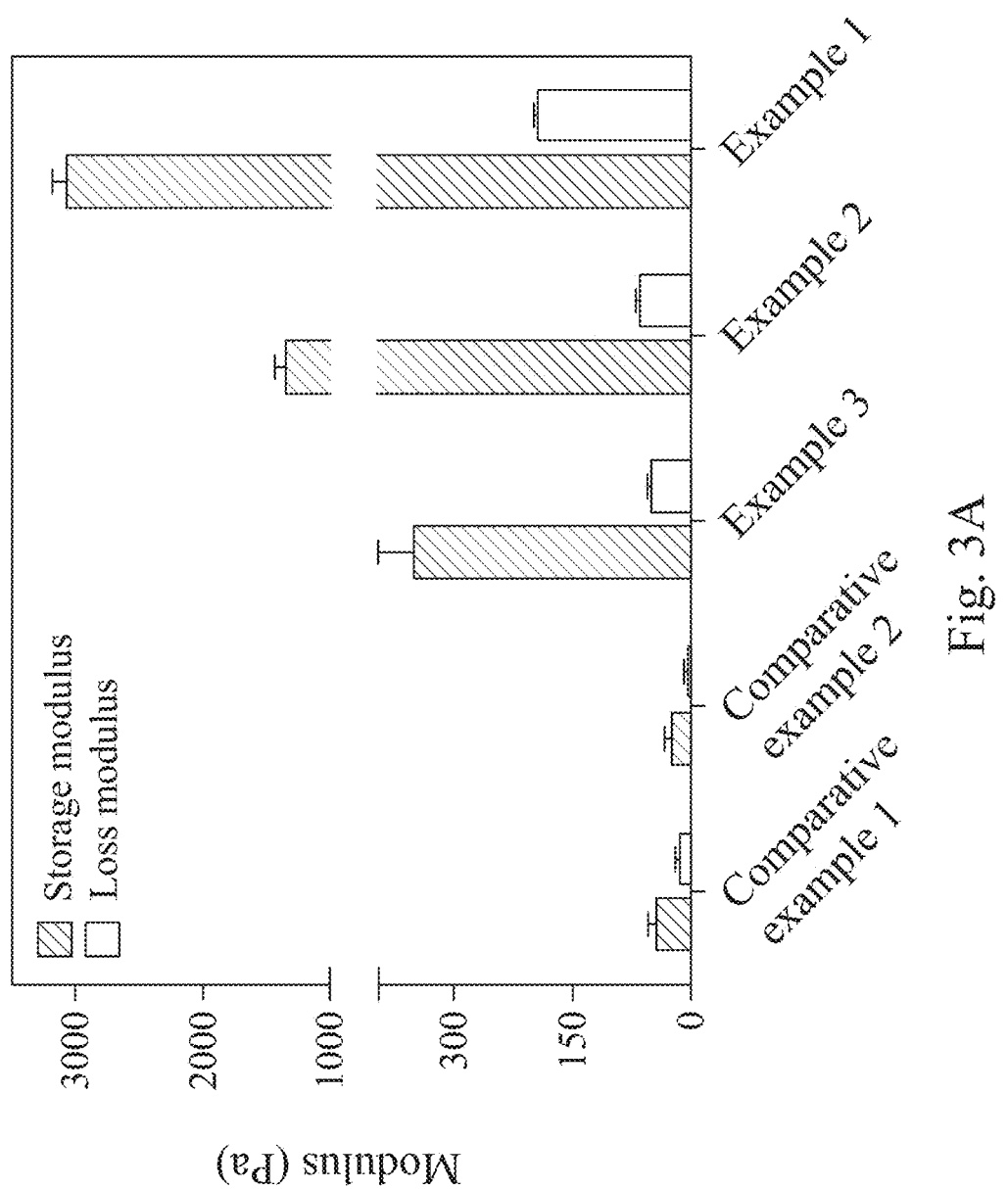
FIG. 3A is a result histogram showing the rheological properties of the injectable and shearing-thinning microbeads gel according to the present disclosure.

Please refer to FIG. 3A, which is a result histogram showing the rheological properties of the injectable and shearing-thinning microbeads gel according to the present disclosure. As shown in FIG. 3A, all the storage modulus and the loss modulus of the injectable and shearing-thinning microbeads gels of Example 1 to Example 3 are high, but both of the storage modulus of Comparative example 1 and Comparative example 2 are less than 100 Pa, wherein the storage modulus of Example 1 is 3100 Pa, the storage modulus of Example 3 is 350 Pa, which are 17.5 times larger and 155 times larger than the storage modulus of Comparative example 2 (Pa=20), respectively. Accordingly, the injectable and shearing-thinning microbeads gel of the present disclosure has an excellent elasticity and a proper viscously, and the gel strength thereof can be adjusted to 30 Pa to 3100 Pa by different mixing ratio of the first gel microspheres and the second gel microspheres.

In the present experiment, the shear-thinning property of the injectable and shearing-thinning microbeads gel of the present disclosure (at p/n=1/1) was validated by the multi-cycle step strain oscillatory measurements at constant frequency of 1 Hz.

Figure 3B:
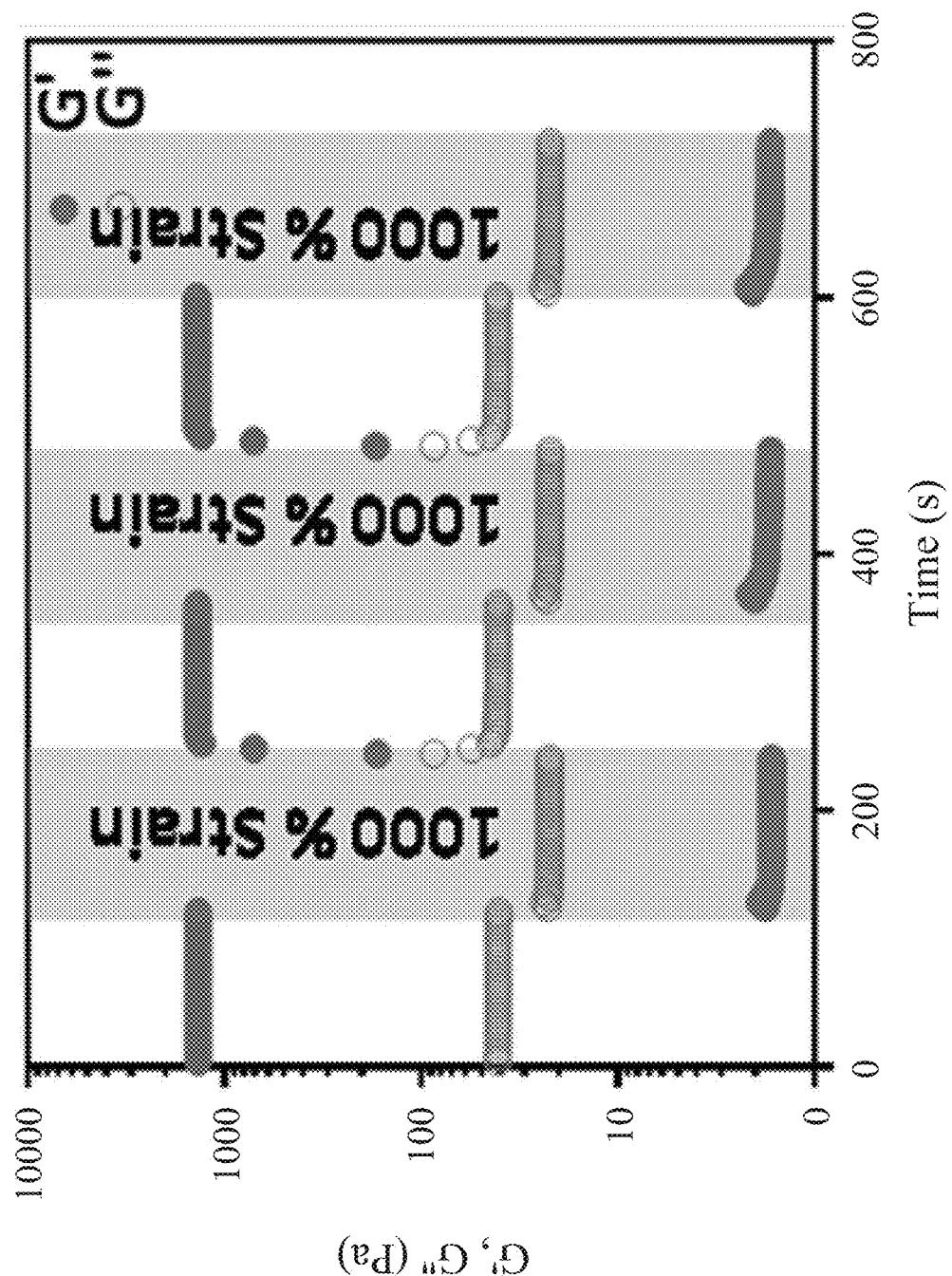
FIG. 3B is a result histogram of storage modulus and loss modulus of the shear-thinning property of the injectable and shearing-thinning microbeads gel according to the present disclosure.

Please refer to FIG. 3B, which is a result histogram of storage modulus and loss modulus of the shear-thinning property of the injectable and shearing-thinning microbeads gel according to the present disclosure. As shown in FIG. 3B, at the first cycle of the injectable and shearing-thinning microbeads gel of the present disclosure exhibited an elastic and loss modulus of 1,500 Pa and 42 Pa, respectively, indicating the elastic regime dominated over the viscous regime. At 1% strain of oscillatory shear, storage modulus is stronger than loss modulus, and they performed constantly at the time duration, suggesting the injectable and shearing-thinning microbeads gel of the present disclosure remained intact at low shear strain. Furthermore, with an rapid increase of shear strain to 1,000%, the loss modulus is much higher than storage modulus, implying that the viscous regime dominated over elastic at this time period. On the reversal of shear strain, the elastic regime restored its predominant over the viscous domain. The result significantly confirmed the re-formation ability of the injectable and shearing-thinning microbeads gel of the present disclosure, which also demonstrated the self-healing nature thereof. Furthermore, the repeated high strain up to 1,000% also displayed no obviously loss in moduli upon the abrupt retraction of elastic domain. That is, the injectable and shearing-thinning microbeads gel of the present disclosure regains the original storage modulus and loss modulus within few seconds after deformation because of the rapid adaptable interactions. The repeated oscillatory shear strain of the injectable and shearing-thinning microbeads gel of the present disclosure causes low change in moduli, indicating the excellent self-healing characteristic with a repeatable feature.

Furthermore, it is worth to be noted that the injectable and shearing-thinning microbeads gel of the present disclosure has an adjustable viscosity due to the mixing of the first gel microspheres with positive electric charge and the second gel microspheres with negative electric charge, so that the adjustment range of stiffness of the cell growth scaffold thereof can be further expanded. Therefore, the application range of the injectable and shearing-thinning microbeads gel of the present disclosure can be further enhanced.

2. Evaluate the Average Porosity and the Average Pore Size of the Injectable and Shearing-Thinning Microbeads Gel of the Present Disclosure The average porosity and the average pore size of the injectable and shearing-thinning microbeads gel of the present disclosure are evaluated by the injectable and shearing-thinning microbeads gel of the aforementioned Example 1. Furthermore, the average particle size of the gel microspheres of Example 1 (including the first gel microspheres and the second gel microspheres) are further adjusted so as to evaluated the average porosity and the average pore size of the injectable and shearing-thinning microbeads gel of the present disclosure under different average particle sizes, wherein the average particle sizes of Example 1 are, in order from small to large, 115 μm, 125 μm, 156 μm, 175 μm and 210 μm. In the present test, the injectable and shearing-thinning microbeads gel of the present disclosure is stained by fluorescent staining method, and microscopic fluorescence images thereof are taken by a conjugate focal microscope and are further analyzed so as to evaluated the average porosity and the average pore size of the injectable and shearing-thinning microbeads gel of the present disclosure under different average particle sizes.

Figure 4A:
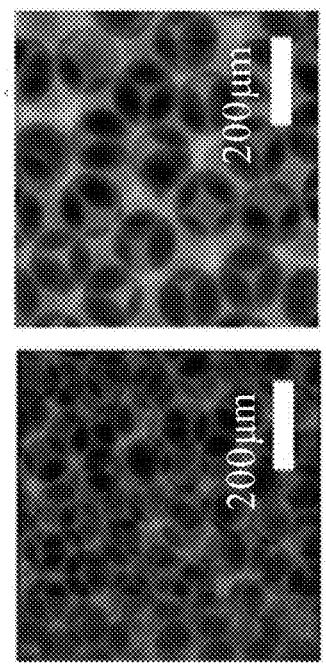
FIG. 4A is a microscope image of the injectable and shearing-thinning microbeads gel of the present disclosure under different particle sizes.
Figure 4B:
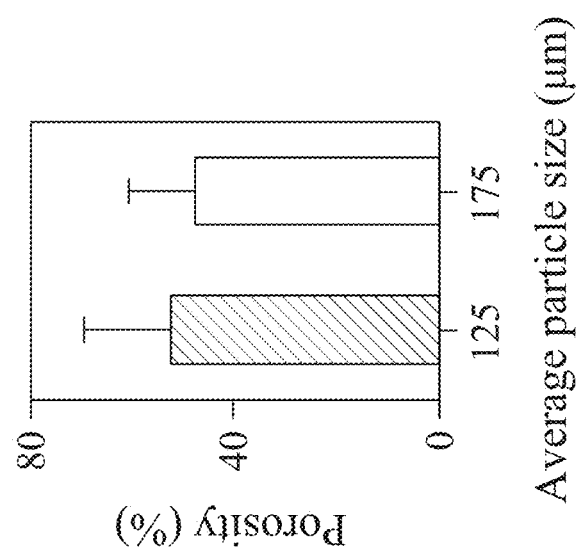
FIG. 4B is a result histogram of the porosity of the injectable and shearing-thinning microbeads gel of FIG. 4A under different particle sizes.

Please refer to FIG. 4A and FIG. 4B. FIG. 4A is a microscope image of the injectable and shearing-thinning microbeads gel of the present disclosure under different particle sizes. FIG. 4B is a result histogram of the porosity of the injectable and shearing-thinning microbeads gel of FIG. 4A under different particle sizes. In detail, FIG. 4A shows, in order from left to right, the microscope images of the gel microspheres having the average particle sizes being 125 μm and 175 μm, respectively. As shown in FIG. 4A and FIG. 4B, the injectable and shearing-thinning microbeads gel of the present disclosure has interconnected and aligned pores in the structure thereof. When the average particle sizes of the gel microspheres are 125 μm and 175 μm, all of the average porosities thereof are larger than 50%. Therefore, the injectable and shearing-thinning microbeads gel of the present disclosure has excellent pore formation ability.

Figure 5A:
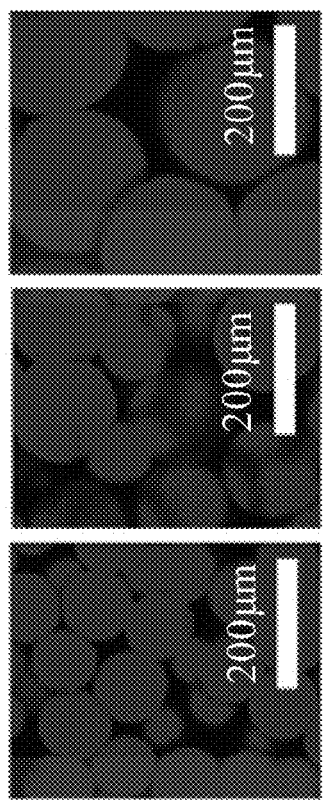
FIG. 5A is another microscope image of the injectable and shearing-thinning microbeads gel of the present disclosure under different particle sizes.
Figure 5B:
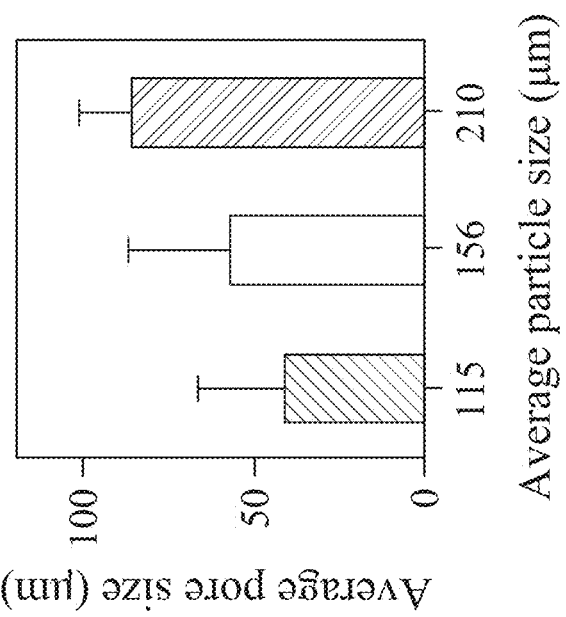
FIG. 5B is a result histogram of the average pore size of the injectable and shearing-thinning microbeads gel of FIG. 5A under different particle sizes.

Please refer to FIG. 5A and FIG. 5B. FIG. 5A is another microscope image of the injectable and shearing-thinning microbeads gel of the present disclosure under different particle sizes. FIG. 5B is a result histogram of the average pore size of the injectable and shearing-thinning microbeads gel of FIG. 5A under different particle sizes. In detail, FIG. 5A shows, in order from left to right, the microscope images of the gel microspheres having the average particle sizes being 115 μm, 156 μm and 210 μm, respectively. As shown in FIG. 5A, the first gel microspheres and the second gel microspheres of the injectable and shearing-thinning microbeads gel of the present disclosure are tightly stacked on each other under the premise that average particle sizes thereof are the same. When the average particle sizes of the gel microspheres are 115 μm, 156 μm and 210 μm, the average pore sizes are 40.8 μm, 57.1 μm and 85.5 μm, respectively. Accordingly, not only the injectable and shearing-thinning microbeads gel of the present disclosure has excellent pore formation ability, but the pore size thereof can be adjusted by adjusting the particle size of the gel microspheres according to actual needs. Therefore, the injectable and shearing-thinning microbeads gel of the present disclosure has the potential to promote a tissue repair to a subject in need for the tissue repair.

Furthermore, in the injectable and shearing-thinning microbeads gel of the present disclosure, the first gel microspheres and the second gel microspheres with the same particle sizes are stacked and attract to each other by the electrostatic attraction thereof so as to form an interconnected pore network near to 100%. Therefore, it is favorable for effectively improving the shortcomings of the insufficient oxygen and nutrient exchange of the conventional hydrogels.

III. Estimate the Biocompatibility of the Injectable and Shearing-Thinning Microbeads Gel of the Present Disclosure The biocompatibility of the injectable and shearing-thinning microbeads gel of the present disclosure is estimated by the cell viability of the human adipose stem cells (hADSC), the Schwann cells and the fibroblasts as well as the ability to promote cell proliferation thereof.

1. Cell Viability Test of the Injectable and Shearing-thinning Microbeads Gel of the Present Disclosure The cell viability test of the injectable and shearing-thinning microbeads gel of the present disclosure is performed by using the injectable and shearing-thinning microbeads gel of the aforementioned Example 2. In the present test, the injectable and shearing-thinning microbeads gel of Example 2 is cut into gel sheets with a thickness of 2 mm and then placed in different wells of the cell culture dish, respectively. Then, different cell culture medium including $3 \times 10^6$ of the human adipose stem cells, the Schwann cells and the fibroblasts are injected into the gel sheets of different wells at different angles, respectively, and incubated at 37° C., 5% $CO_2$ for 24 hours. After incubating for 24 hours, 100 µL of MTT reagent is added into each of the wells and incubated at 37° C. for 4 hours, and then an absorbance at 570 nm thereof is measured by a spectrophotometer and further converted into the data of the cell viability thereof.

Furthermore, the present test also includes the aforementioned Comparative example 1 and Comparative example 2 so as to further illustrate the biocompatibility of the injectable and shearing-thinning microbeads gel of the present disclosure.

Figure 6:
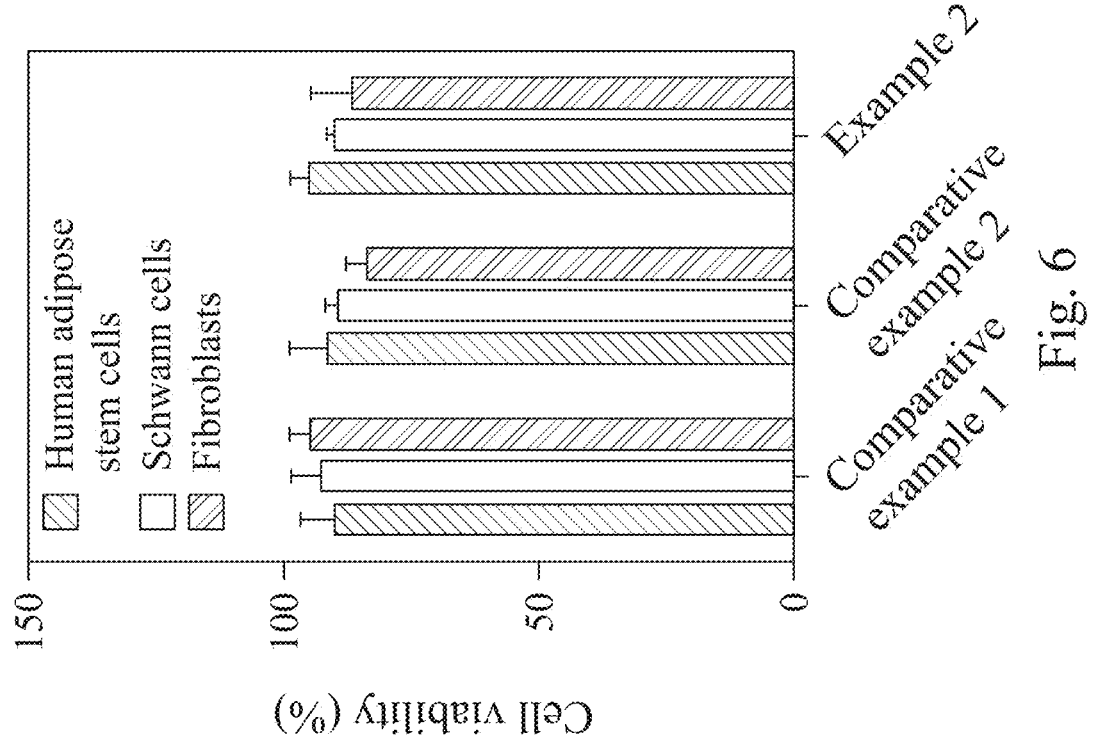
FIG. 6 is a result histogram of the cell viability of different cells using the injectable and shearing-thinning microbeads gel of the present disclosure as a culture substrate and incubating for 24 hours.

Please refer to FIG. 6, which is a result histogram of the cell viability of different cells using the injectable and shearing-thinning microbeads gel of the present disclosure as a culture substrate and incubating for 24 hours. As shown in FIG. 6, all of the cell viability data of the human adipose stem cells, the Schwann cells and the fibroblasts incubated in the injectable and shearing-thinning microbeads gel of Example 2 for 24 hours are larger than 90%, wherein the cell viability data of the human adipose stem cells is best and has a better performance compared to Comparative example 1 and Comparative example 2. Therefore, the injectable and shearing-thinning microbeads gel of the present disclosure has excellent biocompatibility and can be used to promote a tissue repair to a subject in need for the tissue repair.

2. Estimate the Ability to Promote Cell Proliferation of the Injectable and Shearing-Thinning Microbeads Gel of the Present Disclosure The ability to promote cell proliferation of the injectable and shearing-thinning microbeads gel of the present disclosure is performed by using the injectable and shearing-thinning microbeads gel of the aforementioned Example 2 and Comparative example 3 including a conventional non-porous hydrogel.

In the present test, the human adipose stem cells, the Schwann cells and the fibroblasts respectively incubated in the injectable and shearing-thinning microbeads gel of Example 2 and the non-porous hydrogel of Comparative example 3 for different times are treated by 3.7% of formaldehyde for 15 minutes. Next, 0.1% of Triton-X100 is added therein and reacted for 10 minutes, and then fluorescently labeled phalloidin with a dilution ratio being 1:300 is added therein for reacting for 1 hour. Then, DAPI with a dilution ratio being 1:500 is added therein for reacting for 5 minutes and then washed by saline, and then the aforementioned cells are observed by fluorescence microscopy. Specifically, the cell the incubation times of Example 2 are 3 hours, 2 days and 6 days, and the cell the incubation times of Comparative example 3 are 3 hours and 4 days.

Figure 7:
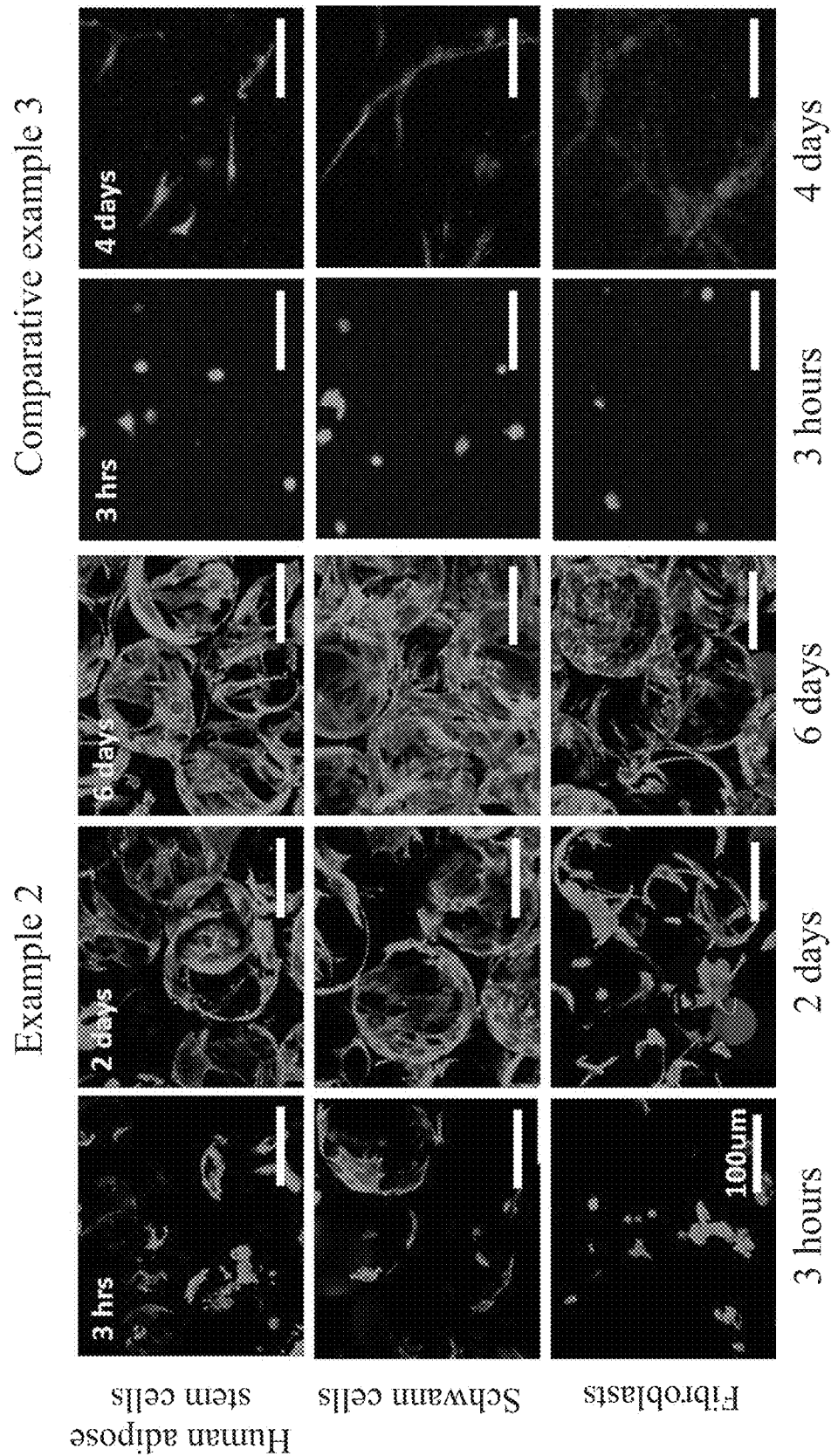
FIG. 7 is a tissue staining image diagram of different cells using the injectable and shearing-thinning microbeads gel of the present disclosure as a culture substrate and incubating for different incubation time.

Please refer to FIG. 7, which is a tissue staining image diagram of different cells using the injectable and shearing-thinning microbeads gel of the present disclosure as a culture substrate and incubating for different incubation time, wherein the blue fluorescent part presents the nucleus, and the green fluorescent part presents the cytoskeleton. As shown in FIG. 7, under the premise that the culture medium of all of the human adipose stem cells, the Schwann cells and the fibroblasts are without additional bioactive factors such as attached proteins, after incubating for 3 hours, the human adipose stem cells, the Schwann cells and the fibroblasts begin to attach to the injectable and shearing-thinning microbeads gel of Example 2 and proliferate along the increase of the incubation time. After incubating for 6 days continuously, all of the human adipose stem cells, the Schwann cells and the fibroblasts can growth tightly in the injectable and shearing-thinning microbeads gel of Example 2. However, compared to the non-porous hydrogel of Comparative example 3, the human adipose stem cells, the Schwann cells and the fibroblasts cannot attach on the surfaces of the non-porous hydrogel effectively after incubating for 3 hours and cannot proliferate thereon effectively after incubating for 6 days.

Furthermore, in the present test, the human adipose stem cells, the Schwann cells and the fibroblasts using the injectable and shearing-thinning microbeads gel of the present disclosure as the culture substrate and incubating for different incubation time are respectively analyzed by the flow cytometry for analyzing the number of cells proliferating with incubation time so as to further estimate the biocompatibility of the injectable and shearing-thinning microbeads gel of the present disclosure.

Figure 8:
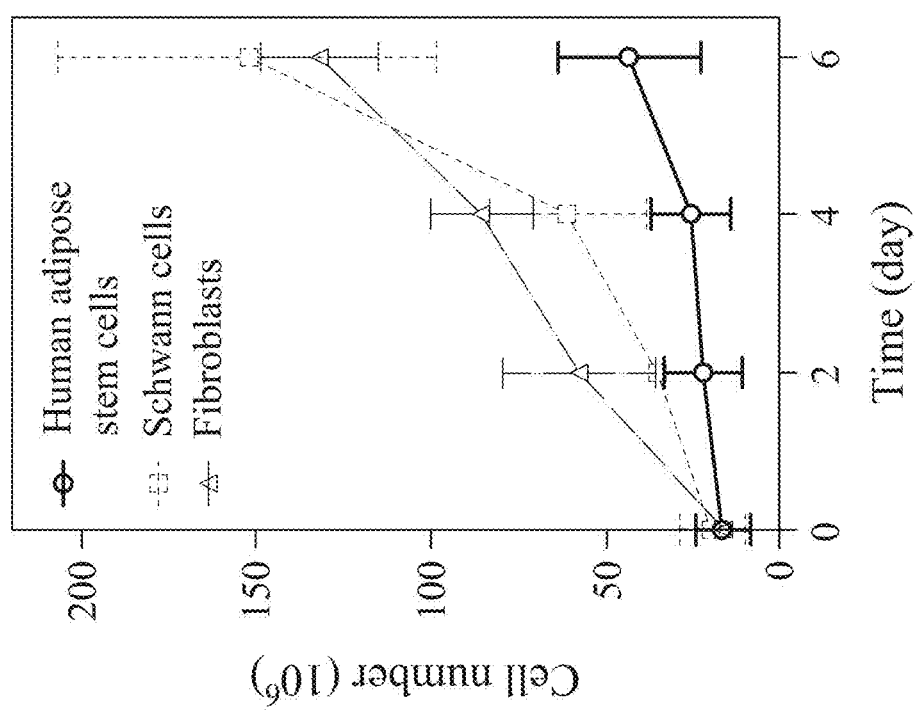
FIG. 8 is a result histogram of the cell proliferation of different cells using the injectable and shearing-thinning microbeads gel of the present disclosure as a culture substrate and incubating for different incubation time.

Please refer to FIG. 8, which is a result histogram of the cell proliferation of different cells using the injectable and shearing-thinning microbeads gel of the present disclosure as a culture substrate and incubating for different incubation time. As shown in FIG. 8, all of the human adipose stem cells, the Schwann cells and the fibroblasts have a constant and continuous proliferation being incubated in the injectable and shearing-thinning microbeads gel of Example 2 for 6 days, wherein the proliferation performance of the Schwann cells and the fibroblasts are the best, and the doubling times (DT) thereof are 2.5 days and 1.5 days, respectively.

To sum up the aforementioned results, the injectable and shearing-thinning microbeads gel of the present disclosure has excellent biocompatibility and good average porosity, thus it is favorable for cells to attach and proliferate therein. Therefore, the injectable and shearing-thinning microbeads gel of the present disclosure can be used to promote a tissue repair to a subject in need for the tissue repair and is suitable for applying to related fields such as tissue engineering or regenerative medicine.

IV. Estimate the Ability to Promote Nerve Cell Repair of the Injectable and Shearing-Thinning Microbeads Gel of the Present Disclosure The ability to promote nerve cell repair of the injectable and shearing-thinning microbeads gel of the present disclosure is estimated by transplanting a nerve conduit of Example 4 including the injectable and shearing-thinning microbeads gel of the present disclosure to the sciatic nerve damage area of the hind limb of a rat (that is, using the nerve conduit of Example 4 to connect the damage gap between the sciatic nerve) and then measuring strength and function of the axons sections of the regenerated sciatic nerve after being transplanted for 7 days, 30 days and 60 days. In detail, in the nerve conduit of Example 4, nerve growth factors (NGF) are packaged in the first gel microspheres and the second gel microspheres of the injectable and shearing-thinning microbeads gel of the present disclosure so as to form a nerve conduit having a concentration gradient of nerve growth factors for the following test.

Furthermore, the present test further includes Comparative example 4 including a conventional nerve conduit so as to illustrate the ability to promote nerve cell repair of the injectable and shearing-thinning microbeads gel of the present disclosure.

1. Estimate the Nerve Fiber Strength and Growth Status of the Regenerated Sciatic Nerve The nerve fiber strength and growth status of the regenerated sciatic nerve are estimated by the ability to promote nerve cell repair of the nerve conduit including the injectable and shearing-thinning microbeads gel of the present disclosure. In the present test, the regenerated sciatic nerve is divided to the stump section of axons (that is, breakage area of the sciatic nerve), the proximal section of axons, the middle section of axons and the distal section of axons according to the distance away from the trunk of rat. Thus, different axons sections are used to estimating the nerve fiber strength and growth status of the regenerated sciatic nerve in the present test.

Figure 9B:
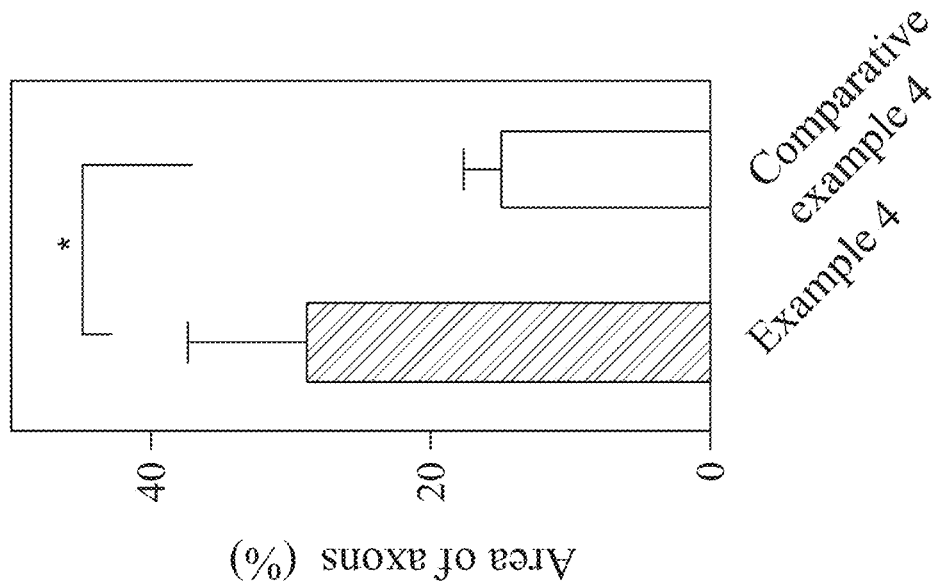
FIG. 9B is a result histogram of the growth of the distal section of the axons of the regenerated sciatic nerve in the nerve conduit of Example 4 of the present disclosure which is transplanted into the hind limb of a rat for 7 days.
Figure 9A:
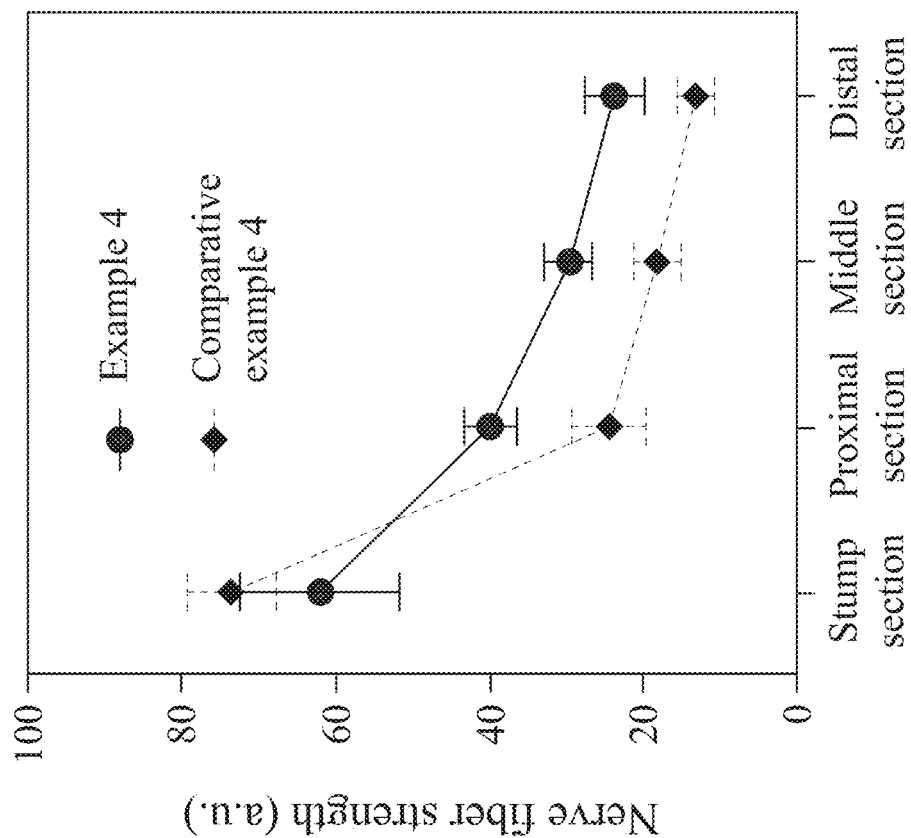
FIG. 9A is a result histogram of the nerve fiber strength of the regenerated sciatic nerve in different axons sections of the nerve conduit of Example 4 of the present disclosure which is transplanted into the hind limb of a rat for 7 days.

Please refer to FIG. 9A, which is a result histogram of the nerve fiber strength of the regenerated sciatic nerve in different axons sections of the nerve conduit of Example 4 of the present disclosure which is transplanted into the hind limb of a rat for 7 days. As shown in FIG. 9A, after the nerve conduit of Example 4 is transplanted for 7 days, the nerve fiber strength of the regenerated sciatic nerve decreases progressively from the stump section of axons of the regenerated sciatic nerve to the distal section of axons thereof. It shows that the sciatic nerve can grow stably in the nerve conduit of Example 4, and the nerve fiber strength of each of the axons sections of the regenerated sciatic nerve in the nerve conduit of Example 4 is greater than the nerve fiber strength of the regenerated sciatic nerve in the nerve conduit of Comparative example 4.

Please refer to FIG. 9B, which is a result histogram of the growth of the distal section of the axons of the regenerated sciatic nerve in the nerve conduit of Example 4 of the present disclosure which is transplanted into the hind limb of a rat for 7 days. As shown in FIG. 9B, after the nerve conduit of Example 4 being transplanted to the sciatic nerve damage area of the hind limb of the rat, the percentage of the distal section of axons of the regenerated sciatic nerve growing into the nerve conduit of Example 4 is significantly higher than Comparative example 4. It shows that the nerve conduit of Example 4 is more suitable for promoting the regeneration of the sciatic nerve compared to Comparative example 4.

2. Analyze the Nerve Function, the Nerve Conduction Velocity and the Compound Action Potential of the Regenerated Sciatic Nerve The ability to promote nerve cell repair of the nerve conduit including the injectable and shearing-thinning microbeads gel of the present disclosure and the function of the regenerated sciatic nerve thereof are estimated by transplanting the nerve conduit of Example 4 to the sciatic nerve damage area of the hind limb of a rat and then measuring the sciatic nerve function index (SFI) of the regenerated sciatic nerve. Furthermore, the present test furthermore includes Control group 1 which transplants an autologous nerve so as to illustrate the ability to promote nerve cell repair of the nerve conduit including the injectable and shearing-thinning microbeads gel of the present disclosure.

Figure 10A:
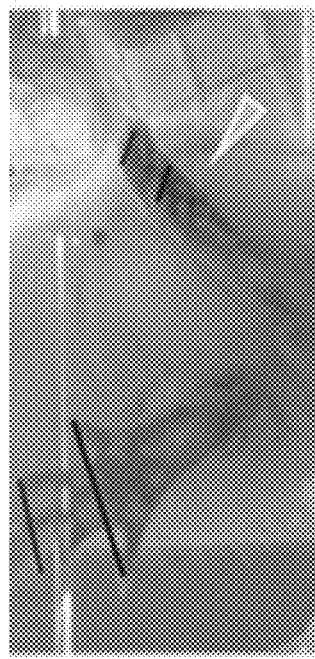
FIG. 10A is an image of the hind limb of a rat that the nerve conduit of Example 4 of the present disclosure is transplanted therein for 30 days.
Figure 10A:
Figure 10B:
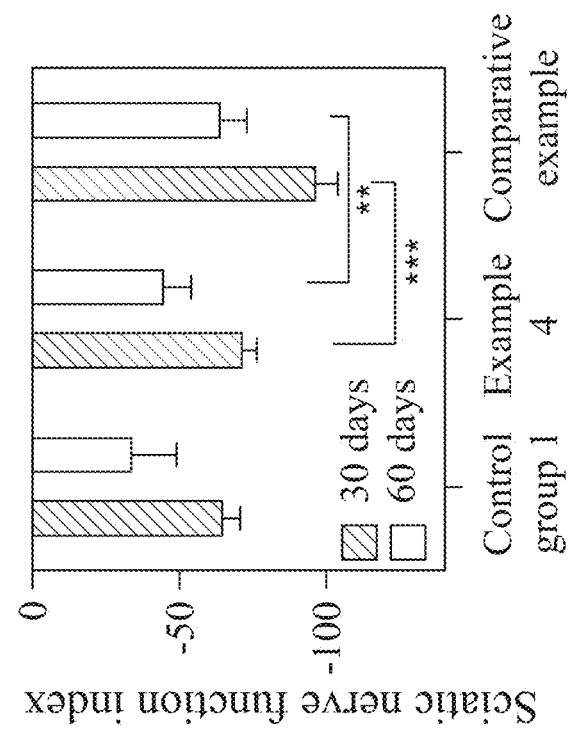
FIG. 10B is a result histogram of sciatic function index of the nerve conduit of Example 4 of the present disclosure which is transplanted into the hind limb of a rat for 30 days and 60 days.

Please refer to FIG. 10A and FIG. 10B. FIG. 10A is an image of the hind limb of a rat that the nerve conduit of Example 4 of the present disclosure is transplanted therein for 30 days. FIG. 10B is a result histogram of sciatic function index of the nerve conduit of Example 4 of the present disclosure which is transplanted into the hind limb of a rat for 30 days and 60 days. As shown in FIG. 10A, the nerve conduit of Example 4 and the nerve conduit of Comparative example 4 are respectively transplanted to the hurt left hind paw of the rat (that is, the paw of the hind limb near to right side of the image). After the nerve conduit of Example 4 being transplanted to the hind limb of the rat for 30 days, the degrees of expansion of the toes of the hurt hind paw of the rat is greater than that of the nerve conduit of Comparative example 4. As shown in FIG. 10B, after the nerve conduit of Example 4 being transplanted for 30 days and 60 days, the sciatic nerve function index thereof is similar with the sciatic nerve function index of Control group 1 and better than the sciatic nerve function index of Comparative example 4. It shows that the nerve conduit including the injectable and shearing-thinning microbeads gel of the present disclosure has excellent effect to promote the repair of the hurt sciatic nerve.

Furthermore, the nerve conduction velocity and the compound action potential of the regenerated sciatic nerve are estimated by transplanting the nerve conduit of Example 4 of the hind limb of the rat and then measuring the nerve conduction velocity and the action potential of the regenerated sciatic nerve so as to further estimate the ability to promote nerve cell repair of the nerve conduit including the injectable and shearing-thinning microbeads gel of the present disclosure. Moreover, the present test further includes the aforementioned Control group 1 and Control group 2 including a rat having a undamaged sciatic nerve so as to further illustrate the ability to promote nerve cell repair of the nerve conduit including the injectable and shearing-thinning microbeads gel of the present disclosure.

Figure 11B:
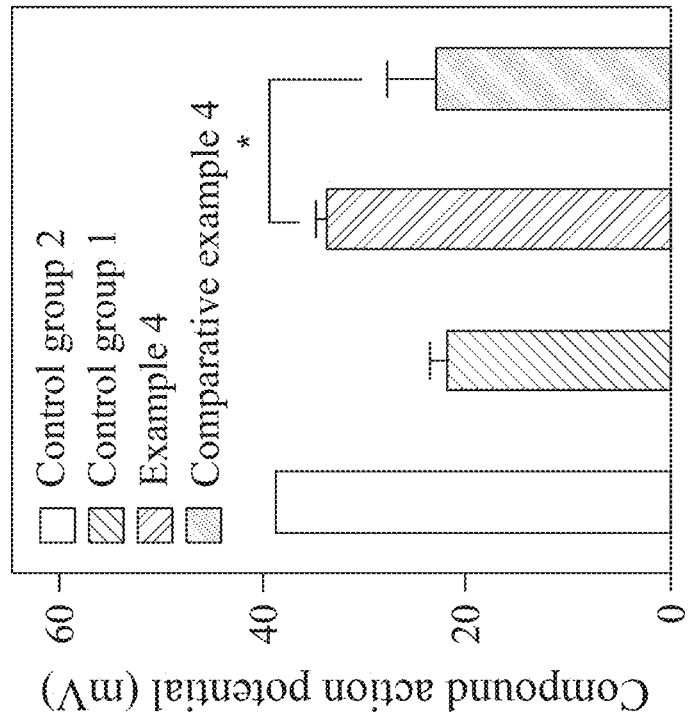
FIG. 11B is a result histogram of compound action potential of the sciatic nerve in the nerve conduit of Example 4 of the present disclosure which is transplanted into the hind limb of a rat for 60 days.
Figure 11A:
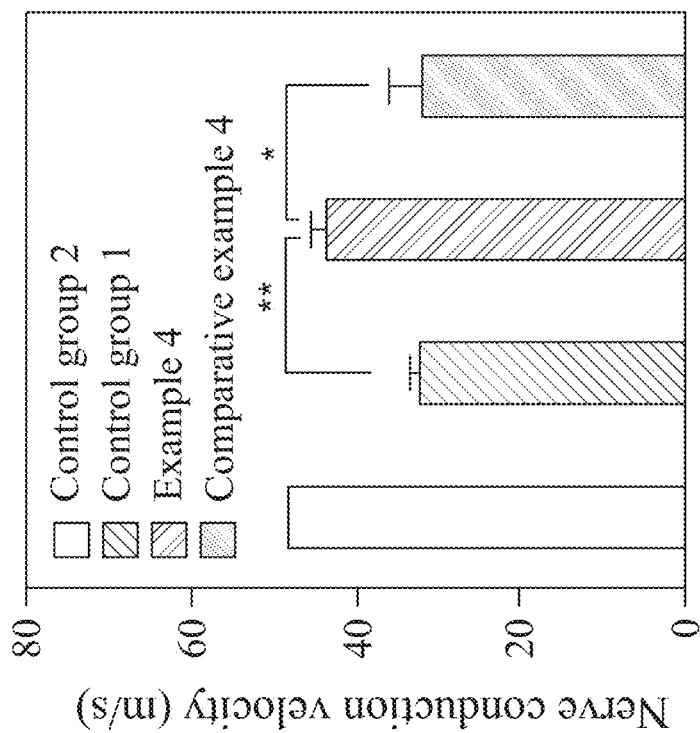
FIG. 11A is a result histogram of nerve conduction velocity of the sciatic nerve in the nerve conduit of Example 4 of the present disclosure which is transplanted into the hind limb of a rat for 60 days.

Please refer to FIG. 11A and FIG. 11B. FIG. 11A is a result histogram of nerve conduction velocity of the sciatic nerve in the nerve conduit of Example 4 of the present disclosure which is transplanted into the hind limb of a rat for 60 days. FIG. 11B is a result histogram of compound action potential of the sciatic nerve in the nerve conduit of Example 4 of the present disclosure which is transplanted into the hind limb of a rat for 60 days. As shown in FIG. 11A, after the nerve conduit of Example 4 being transplanted to the hind limb of the rat for 60 days, the nerve conduction velocity of the sciatic nerve thereof is significantly better than the nerve conduction velocities of Comparative example 4 and Control group 1 and is close to the nerve conduction velocity of Control group 2. As shown in FIG. 11B, after the nerve conduit of Example 4 being transplanted to the hind limb of the rat for 60 days, the compound action potential of the sciatic nerve thereof is significantly greater than the compound action potential of Comparative example 4.

As shown in the aforementioned results, the nerve conduit including the injectable and shearing-thinning microbeads gel of the present disclosure has an ability to promote the repair of the nerve cells, so that the injectable and shearing-thinning microbeads gel of the present disclosure has a potential to promote a nerve cell growth of a subject in need for a treatment of a nerve damage.

To sum up, the injectable and shearing-thinning microbeads gel of the present disclosure and the method for preparing the injectable and shearing-thinning microbeads gel can be applied by an injection method and used directly and has excellent and shearing-thinning ability by mixing the first gel microspheres and the second gel microspheres having opposite electric charges. Furthermore, because the method for preparing the injectable and shearing-thinning microbeads gel of the present disclosure uses an acrylic acid compound or a derivative thereof and materials with high biocompatibility as the materials of the first gel microspheres and the second gel microspheres, it is favorable for preventing the toxicity of the material generated from the materials to the cells and is favorable for mass production. Accordingly, the use security and application bread of the injectable and shearing-thinning microbeads gel made by the method for preparing the injectable and shearing-thinning microbeads gel of the present disclosure can be enhanced. Moreover, because the injectable and shearing-thinning microbeads gel of the present disclosure has high biocompatibility and an ability to promote cell proliferation, the injectable and shearing-thinning microbeads gel of the present disclosure can be used to promote a tissue repair to a subject in need for the tissue repair and can used as a biomedical material for promoting cell proliferation and tissue repair, and it has the potential to be further applied to the preparation of pharmaceutical compositions for promoting the growth of nerve cells, thereby achieving an objective of providing an efficient and safe adjuvant treatment to the human body.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

The invention claimed is:

1. A method for preparing an injectable and shearing-thinning microbeads gel, comprising:
   performing a first gel microsphere preparing step, wherein the first gel microsphere preparing step comprises:
   providing a first solution, wherein the first solution is used as a water phase and comprises a first component and a second component, the first component comprises an acrylic acid compound or a derivative thereof, and the second component comprises a chitosan oligomer or a silk;
   providing a first oil-phase solution; and
   performing a first water-in-oil emulsification by mixing the first solution and the first oil-phase solution so as to form a plurality of first gel microspheres;
   wherein an average particle size of the first gel microspheres ranges from 30 µm to 500 µm;
   performing a second gel microsphere preparing step, wherein the second gel microsphere preparing step comprises: providing a second solution, wherein the second solution is used as a water phase and comprises a third component and a fourth component, the third component comprises an acrylic acid compound or a derivative thereof, and the fourth component comprises a gelatin, a hyaluronic acid or an alginate;
   providing a second oil-phase solution; and
   performing a second water-in-oil emulsification by mixing the second solution and the second oil-phase solution so as to form a plurality of second gel microspheres;
   wherein an average particle size of the second gel microspheres ranges from 30 µm to 500 µm; and
   performing a mixing step, wherein the mixing step mixes the first gel microspheres, the second gel microspheres and an aqueous solution so as to obtain the injectable and shearing-thinning microbeads gel;
   wherein each of the first gel microspheres has a first electric charge, each of the second gel microspheres has a second electric charge, and the first electric charge is opposite to the second electric charge.

2. The method of claim 1, wherein the acrylic acid compound or a derivative thereof comprises methacrylic acid, methacrylic anhydride or glycidyl methacrylate.

3. The method of claim 1, wherein the first gel microspheres and the second gel microspheres of the injectable and shearing-thinning microbeads gel are contained in a volume ratio of 1:0.5 to 1:6.

4. The method of claim 1, wherein the method is performed in a microfluidic system.

5. The method of claim 1, wherein a gel strength of the injectable and shearing-thinning microbeads gel ranges from 30 Pa to 3100 Pa.

6. The method of claim 1, wherein an average porosity of the injectable and shearing-thinning microbeads gel ranges from 35% to 50%.

7. The method of claim 1, wherein an average pore size of the injectable and shearing-thinning microbeads gel ranges from 30 µm to 90 µm.

\* \* \* \* \*